(12) United States Patent  
Jones et al.

(10) Patent No.: US 8,140,172 B1
(45) Date of Patent: Mar. 20, 2012

(54) IMPLANTABLE ANCHOR WITH LOCKING ARM

(75) Inventors: Robert E Jones, McKinney, TX (US); Joy Huang, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 289 days.

(21) Appl. No.: 12/502,068

(22) Filed: Jul. 13, 2009

Related U.S. Application Data

(60) Provisional application No. 61/079,922, filed on Jul. 11, 2008.

(51) Int. Cl.
*A61N 1/05* (2006.01)

(52) U.S. Cl. .................... 607/126; 607/132; 600/375

(58) Field of Classification Search .................. None
See application file for complete search history.

(56) References Cited

U.S. PATENT DOCUMENTS

| | | | | |
|---|---|---|---|---|
| 4,276,882 A * | 7/1981 | Dickhudt et al. | ............... | 607/9 |
| 4,553,961 A * | 11/1985 | Pohndorf et al. | ............ | 604/175 |
| 5,107,856 A * | 4/1992 | Kristiansen et al. | .......... | 607/126 |
| 5,273,053 A * | 12/1993 | Pohndorf | ................... | 607/132 |
| 5,746,722 A * | 5/1998 | Pohndorf et al. | ............ | 604/175 |
| 5,824,032 A * | 10/1998 | Belden | .......................... | 607/126 |
| 5,957,968 A * | 9/1999 | Belden et al. | ................ | 607/126 |
| 6,361,523 B1* | 3/2002 | Bierman | ..................... | 604/174 |
| 6,473,654 B1* | 10/2002 | Chinn | ......................... | 607/126 |
| 7,787,960 B2* | 8/2010 | Lubenow et al. | ............ | 607/116 |
| 7,831,313 B2* | 11/2010 | Lauro | ......................... | 607/126 |
| 7,930,039 B2* | 4/2011 | Olson | ......................... | 607/126 |
| 2011/0004281 A1* | 1/2011 | Jones | ......................... | 607/116 |

\* cited by examiner

*Primary Examiner* — Kennedy Schaetzle (74) *Attorney, Agent, or Firm* — Craig Hoersten; Christopher S. L. Crawford; Peter R. Lando (57) ABSTRACT

There is disclosed various embodiments of an implantable anchor for permanently anchoring a medical lead. The implantable anchor may include a body having a longitudinal lumen, an access opening defined within a side of the body and in communication with the longitudinal lumen, a locking opening defined on an interior surface of the body, an arm having an interior face, the arm rotatably coupled to the body such that the arm is movable from a first position in which the arm covers the access opening to a second position in which the arm does not cover the access opening, and a locking feature protruding from the interior face of the arm and sized to extend into the locking opening.

19 Claims, 9 Drawing Sheets

IMPLANTABLE ANCHOR WITH LOCKING ARM

CROSS-REFERENCE TO RELATED APPLICATIONS

This application claims the benefit of U.S. Provisional Application No. 61/079,922, filed Jul. 11, 2008, which is incorporated herein by reference.

TECHNICAL FIELD

The present application is generally related to an implantable anchor for anchoring an electrical stimulation lead, a drug infusion catheter, an electrical stimulation lead, or other catheter of an implantable medical device system.

BACKGROUND

A number of implantable medical devices have been commercially distributed that allow various medical agents to be controllably infused after implantation of the respective device within a patient. For example, implantable medical devices are used for the infusion of insulin, opiates, antispasmodic drugs, intrahepatic chemotherapy agents, and other therapeutic agents in a number of countries subject to the regulatory requirements of those countries.

There are a number of benefits to the use of implantable infusion devices. For example, when the therapeutic agent is delivered directly to the therapy site (for opiates and baclofen), the amount of the therapeutic agent that is needed is much lower. Side-effects are generally minimized. Also, the therapeutic effect can be significantly greater as compared to intravenous introduction of therapeutic agents (again, for opiates and baclofen). Furthermore, implantable infusion devices eliminate patient overdosing or underdosing due to patient error or limited patient capacity.

Implantable infusion devices typically include a central housing that includes a reservoir to hold the infusate, a septum to allow infusate to be introduced into the reservoir, an energy source to drive the infusate from the reservoir and through an outlet port, and various flow control elements. The central housing portion of the device is typically implanted in a suitable subcutaneous region with the septum positioned immediately below the skin of the patient to facilitate access to the reservoir for refilling purposes.

To deliver the infusate from the reservoir, a catheter is usually attached to the outlet port of the central housing to receive the infusate outflow. The distal end of the catheter is implanted within the patient adjacent to the appropriate therapy site (e.g., at a suitable intrathecal location to allow introduction of an infusate directly into the spinal fluid of the patient). Typically, some mechanism is employed to anchor the catheter so that infusate will continue to be delivered to the appropriate site such as sutures and/or anchoring structures.

Similar anchoring is also used in spinal cord stimulation (SCS) systems. In SCS systems, a pulse generator is typically implanted within a subcutaneous pocket within the patient. An electrical lead is also implanted within the patient. The proximal end of the electrical lead is electrically coupled (either directly or via one or more extensions) to the pulse generator to receive electrical pulses from the pulse generator. The distal end of the electrical lead is positioned with electrodes of the lead disposed within the epidural space of the patient to deliver the electrical pulses to the spinal neural tissue of the patient. The efficacy of the electrical stimulation in treating chronic pain of the patient depends upon applying the electrical pulses to the appropriate neural tissue. Accordingly, it is desired to retain the stimulation lead at a relatively fixed position over time. For that reason, the electrical lead is anchored so that migration of the electrical lead does not occur.

SUMMARY

In one embodiment, there is disclosed various embodiments of an implantable anchor for permanently anchoring a medical lead. In one embodiment, the implantable anchor may include a body having a longitudinal lumen, an access opening defined within a side of the body and in communication with the longitudinal lumen, a locking opening defined on an interior surface of the body, an arm having an interior face, the arm rotatably coupled to the body such that the arm is movable from a first position in which the arm covers the access opening to a second position in which the arm does not cover the access opening, and a locking feature protruding from the interior face of the arm and sized to extend into the locking opening.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 3a is a lateral cross-sectional view of the embodiment illustrated in FIG. 1a.

FIG. 7b is an isometric cross-section view of the embodiment of FIG. 7a.

FIG. 8b is an isometric cross-section view of the embodiment of FIG. 8a.

DETAILED DESCRIPTION

For the purposes of promoting an understanding of the principles of the present invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

Figure 1A:
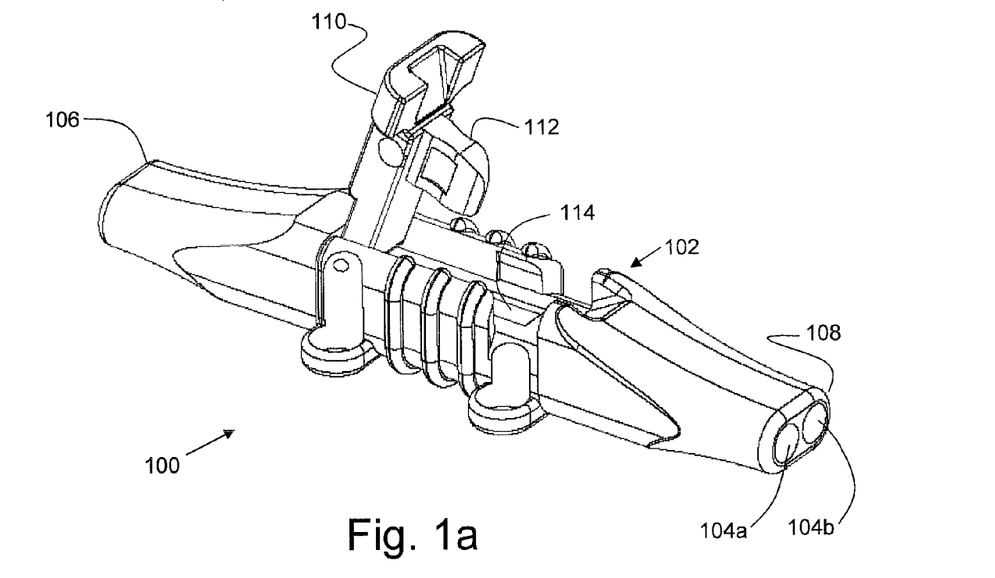
FIG. 1a is an isometric view illustrating one embodiment of an implantable anchor in a first or open configuration.
Figure 1B:
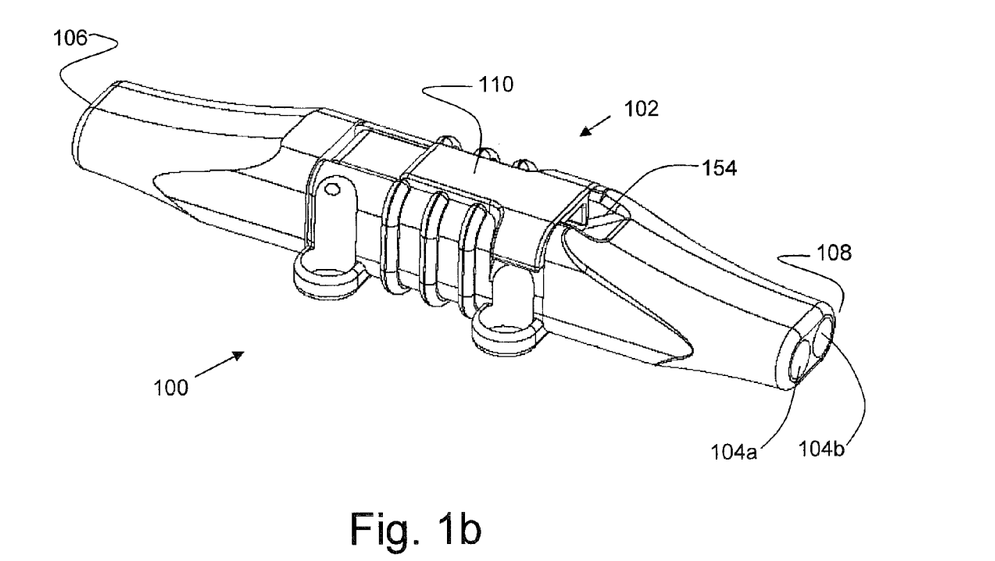
FIG. 1b is an isometric view illustrating one embodiment of an implantable anchor in a second or closed configuration.

FIG. 1a depicts an implantable anchor 100 in a first or open configuration. FIG. 1b depicts the anchor 100 in a second or closed configuration. The anchor 100 may be used for anchoring a drug infusion catheter, an electrical lead, or other catheter (not shown) according to one representative embodiment. For the purpose of this disclosure, the term "lead" is used in a broad manner and should be interpreted to encompass both infusion catheters and stimulation leads.

Figure 9:
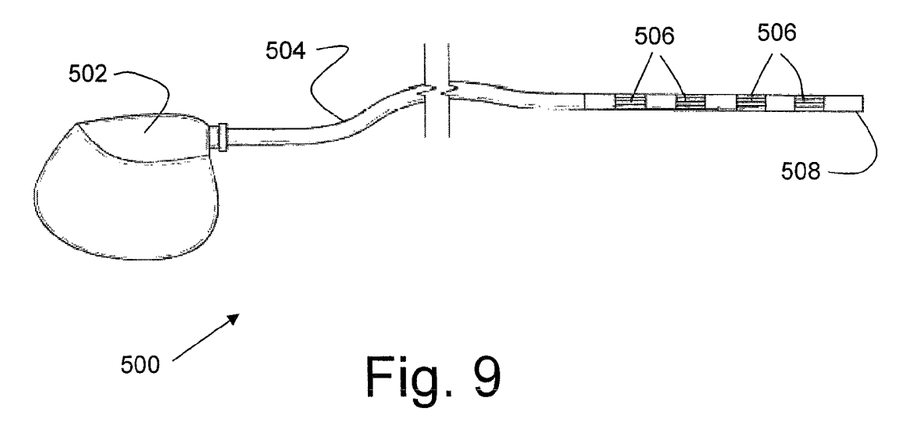
FIG. 9 depicts a conventional neurostimulation system that may utilize an anchor according to at least one representative embodiment.
Figure 10:
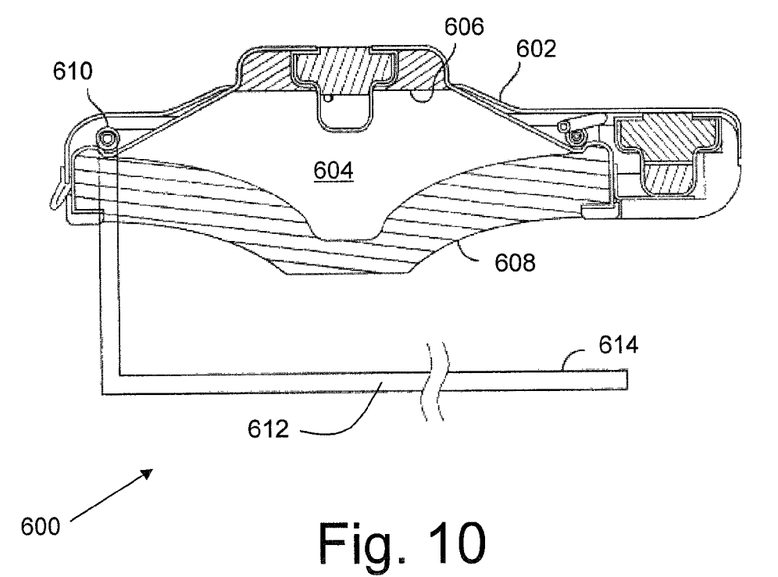
FIG. 10 depicts a conventional drug pump system that may utilize an anchor according to at least one representative embodiment.

The anchor 100 may comprise a longitudinal body 102 having one or more longitudinal lumens defined therein. In the illustrative embodiment, lumens 104a and 104b run longitudinally from a first end 106 to a second end 108 of the longitudinal body 102. Although lumens 104a and 104b are illustrated, any number of lumens may be used and are within the scope of the present invention. As will be explained in greater detail below, the diameter of the longitudinal lumens may be sized to slidingly receive a catheter (not shown) of an implantable infusion system (FIG. 9) or lead of an SCS system (FIG. 10). In use, therefore, the anchor 100 is intended to be placed on the proximal end of two leads and slid over the leads (not shown) until the anchor is properly positioned along the leads.

In certain embodiments, an arm 110 may be moveably coupled to the longitudinal body 102. As will be explained in detail later, the arm 110 may have a locking feature or finger 112, which in the closed configuration illustrated in FIG. 1b, extends through a side opening 114 of the longitudinal body 102 to engage a lead, the longitudinal body or both the lead and the longitudinal body. Such engagement locks the anchor longitudinally in place relative to the lead.

Figure 2:
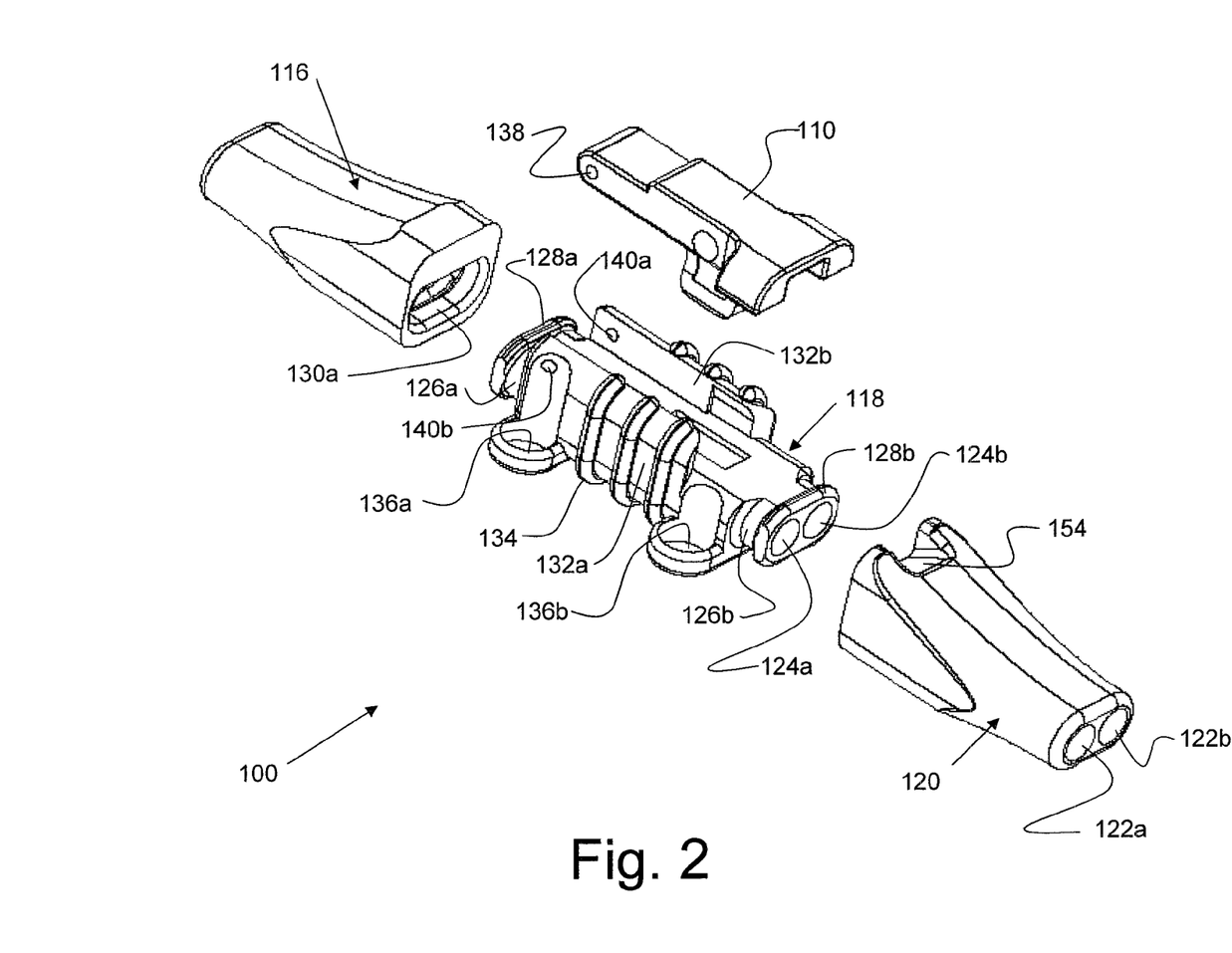
FIG. 2 is an exploded isometric view of the embodiment illustrated in FIGS. 1a and 1b.

FIG. 2 is an exploded view of one embodiment of the anchor 100 depicting various components of this embodiment. As illustrated in FIG. 2, it can be seen that the illustrated embodiment of the longitudinal body 102 may comprise a first end portion 116, a central body portion 118, and a second end portion 120. In certain embodiments, two longitudinal lumens 122a and 122b may be formed within the second end portion 120. Similarly, two longitudinal lumens 124a and 124b may be formed within the central portion 118. Additionally, two longitudinal lumens (not shown) may be formed within the first end portion 116. When the body portions are coupled together such that their respective lumens line up as illustrated in FIG. 1b, the two longitudinal lumens 104a and 104b may be formed by the linear combination of the respective lumens from the central body portion 118 and the end portions 116 and 120.

In certain embodiments, the anchor 100 may be fabricated using any suitable polymer processing technique. The polymer or polymers selected for the anchor 100 are preferably adapted for long term implantation. Biocompatibility and biostability are characteristics for the polymer selection for anchor 100. Also, the polymer preferably possesses a medium to high durometer to maintain the structural characteristics of anchor 100. An example of a suitable polymer for anchor 100 is polyetheretherketone (PEEK), although any biostable, biocompatible polymer having a suitable durometer and a suitable coefficient of friction can be employed.

In one embodiment, a combination of a relatively hard and soft (or flexible) material may be utilized. In this embodiment, the central body 118 may be made from a relatively hard material, such as PEEK. The first end portion 116 and the second end portion 120 may be fabricated from a more compliant material with a lower durometer value, such as silicone. Thus, the first and second end portions 116 and 120 are relatively flexible when compared to the central body 118 and may act as strain relief ports with respect to the central body 118.

In certain embodiments, the central body 118 may have connecting protrusions 126a and 126b extending from each longitudinal end. The connecting protrusions 126a-126b may also have flanges 128a and 128b which extend laterally from the connecting protrusions. Connecting apertures 130a and 130b (only connecting aperture 130a is visible in FIG. 2) defined within the interior ends the first end portion 116 and the second end portion 120 are sized to couple to the connecting protrusions 126a and 126b, respectively. The relatively flexible material of the first and second end portions 116 and 120 allow the connecting apertures 130a and 130b to be pushed over the connecting protrusions 126a and 126b. The first and second end portions 116 and 120 are held into place when the flanges 128a and 128b are seated within a corresponding space (not shown) defined within the connecting apertures 130a and 130b of the first and second end portions.

In other embodiments, the longitudinal body 102 may be formed from a single piece of material. In such embodiments, the end portions may still function as strain relief ports. However, in these embodiments, the relative flexibility of the end portions may be due to geometric properties (such as thickness of the walls, etc.) and not from the different material properties of the component portions. Thus, the term flexibility as used herein may mean deformable (whether by choice of materials or geometry).

In some embodiments, wall portions 132a and 132b of the central body portion 118 may comprise one or more rib structures 134 to assist suturing of anchor 100 to tissue of the patient. In other embodiments, one or more anchor holes 136a and 136b or other similar structures could also be provided in addition to or in place of the rib structures 134.

In certain embodiments, the arm 110 may be coupled to the longitudinal body 102 by means of a pin member (not shown in FIG. 2). In such embodiments, the pin member may be inserted into a lateral bore 138 defined within the arm 110. The ends of the pin member may then be inserted into corresponding bores 140a and 140b defined within the wall portions 132a and 132b and secured in place by a press fit or adhesive joining technique. The arm 110, may therefore rotate from an open position as illustrated in FIG. 1a to the closed position illustrated in FIG. 1b.

Figure 3A:
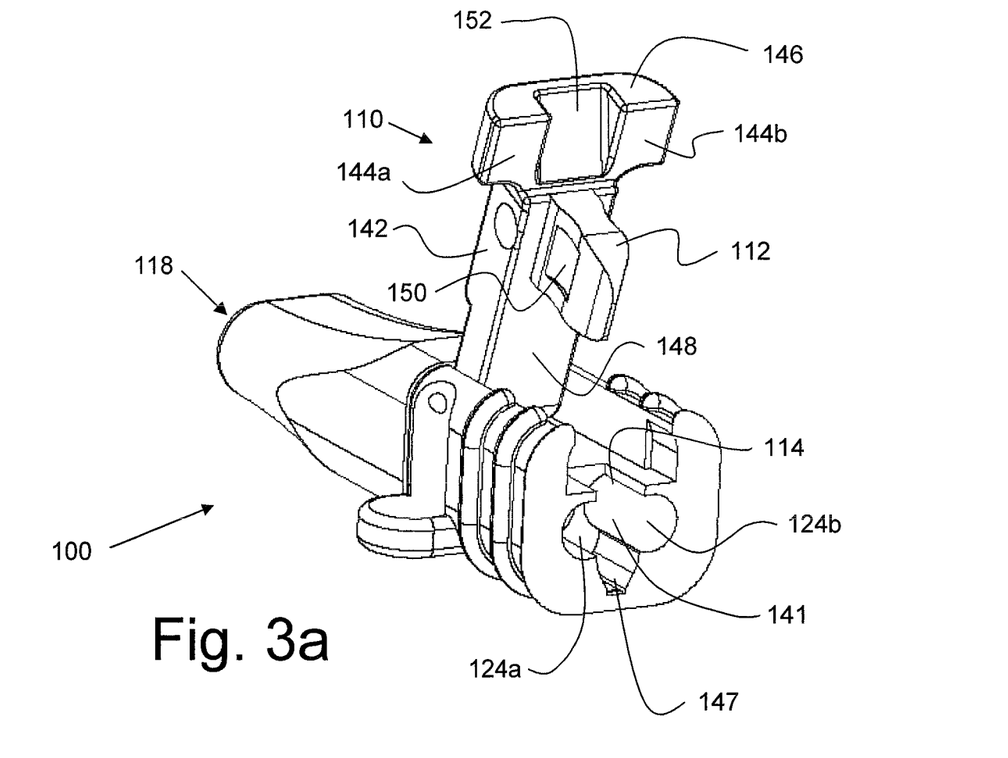
Figure 3B:
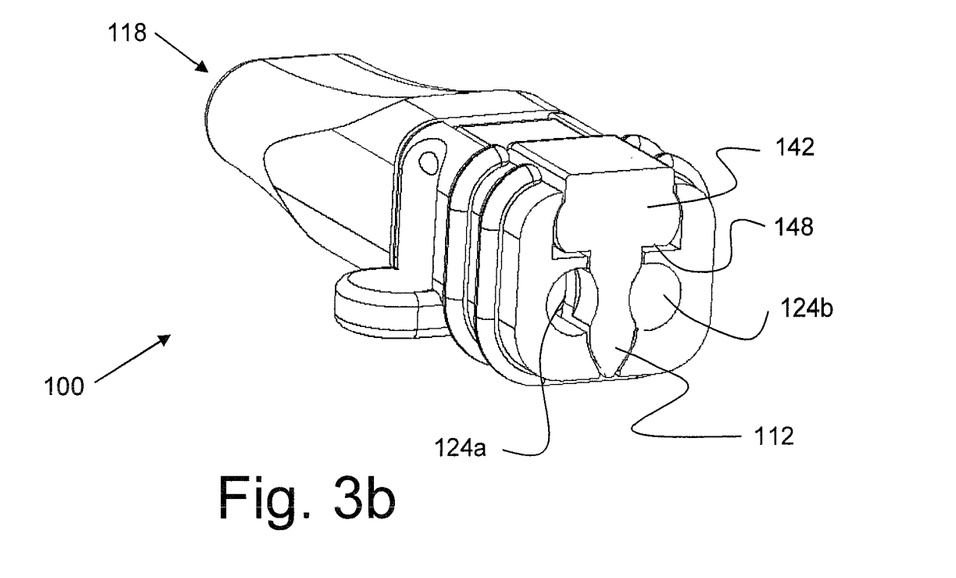
FIG. 3b is a lateral cross-sectional view of the embodiment illustrated in FIG. 1b.

FIG. 3a depicts a lateral cross-sectional view of the anchor 100 in the open or unlocked position. FIG. 3b depicts a lateral cross-sectional view of the anchor 100 in a closed or locked position. In the illustrative embodiment, an interior cavity 141 of the center portion 118 joins the longitudinal lumens 124*a* and 124*b*. Thus, in cross-section, the interior cavity 141 comprises a space occupied by the lumen 124*a*, the lumen 124*b*, and the volume between the lumens.

In certain embodiments, the arm 110 is T-shaped having a longitudinal body 142 and cross members 144*a* and 144*b* at a free end 146. As previously discussed, the locking finger 112 projects from an interior surface or face 148 of the longitudinal body 142. In certain embodiments, the locking finger 112 projects far enough to pass through the access opening 114, through the interior cavity 141 and into a locking opening or indent 147 (as illustrated in FIG. 3*b*).

The diameters of the lumens 124*a* and 124*b* and the size of the interior cavity 141 are sufficiently large to permit the introduction of a lead with little difficulty. Thus, when the arm 110 is in the open position, the anchor 100 may be freely moved along the leads (not shown). However, as illustrated in FIG. 3*b*, when the arm 110 is rotated to the closed position, the finger 112 occupies a portion of the interior cavity 141 and a portion of the space corresponding to the lumens 124*a* and 124*b*. In this closed configuration, the lumens 124*a* and 124*b* are now preferably smaller than the diameters of the leads. Thereby, upon rotation of the arm 110 from an open to a closed position, a compressive force is applied to the lead to cause anchor 100 to hold the lead in place. The lead, therefore, cannot be slipped through the anchor 100 along its longitudinal axis.

In certain embodiments, one or more detents 150 may be formed on at least one surface of the locking finger 112. When the detent 150 is next to a lead made from relatively compliant material, the pressure on the lead causes the compliant material to expand into the detent 150. This expansion also assists in engaging the lead so that the anchor 100 is further locked in place relative to the lead.

In certain embodiments, there may be a first access notch 152 defined at the free end 146 of the arm 110 as illustrated in FIG. 3*a*. There may also be a corresponding access notch 154 defined within the end portion 120 of the anchor body 102 (FIGS. 1 and 2). The access notches 152 and 154 allow a surgeon or other user to unlock the arm 110 by rotating the free end 146 of the arm away from the anchor body 102. Such unlocking may be necessary to adjust the position of the anchor during the surgical procedure.

Figure 4A:
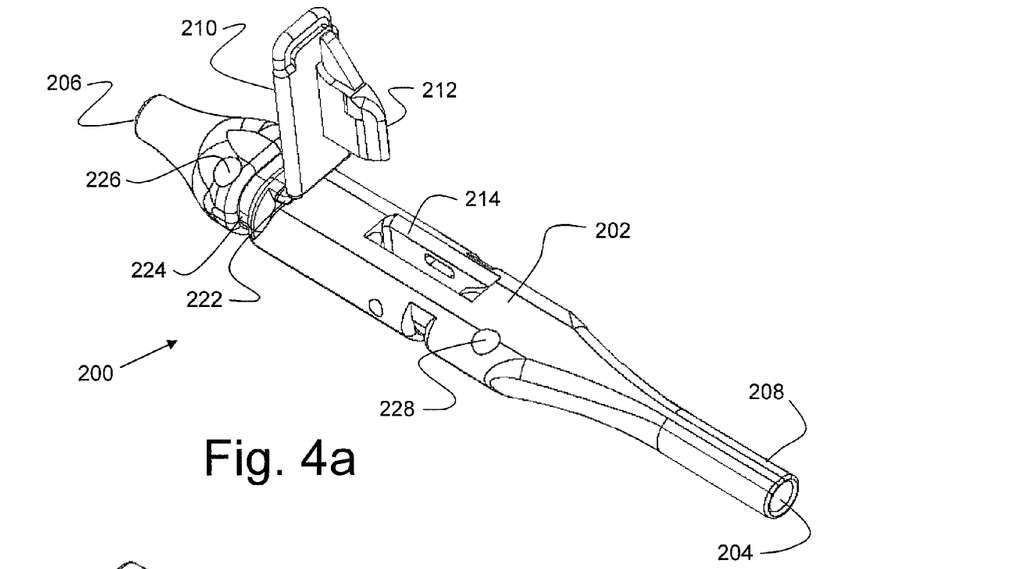
FIG. 4a is an isometric view illustrating one embodiment of an implantable anchor in a first or open configuration.
Figure 4B:
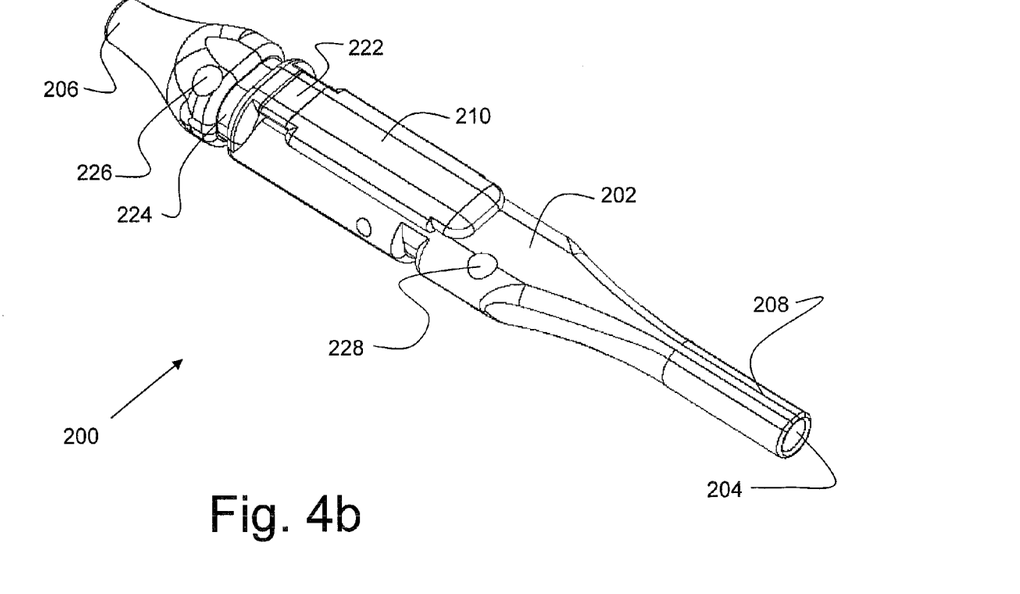
FIG. 4b is an isometric view illustrating one embodiment of an implantable anchor in a second or closed configuration.

FIGS. 4*a* and 4*b* depict an implantable anchor 200 according to an alternative embodiment. The anchor 200 preferably functions in a manner similar to the anchor 100 and, hence, the internal components of the anchor 200 will not be discussed in as much detail. In general, the anchor 200 differs from the anchor 100 in that the anchor 200 comprises a single longitudinal lumen formed from a single piece of material.

FIG. 4*a* depicts the anchor 200 in a first or open configuration. FIG. 4*b* depicts the anchor 200 in a second or closed configuration.

The anchor 200 may comprise a longitudinal body 202 having one or more longitudinal lumens defined therein. In the illustrative embodiment, a lumen 204 runs longitudinally from a first or proximal end 206 to a second or distal end 208 of the longitudinal body 202. Although the lumen 204 is illustrated, any number of lumens may be used and are within the scope of the present invention. As will be explained in greater detail below, the diameter of the longitudinal lumen 204 may be sized to slidingly receive a lead (not shown). In use, therefore, the anchor 200 is intended to be placed on the proximal end of a lead and slid over the lead until the anchor 200 is properly positioned along the lead.

In certain embodiments, an arm 210 may be moveably coupled to the longitudinal body 202. As will be explained in detail later, the arm 210 may have a locking feature or finger 212, which in the closed configuration illustrated in FIG. 4*b*, extends through a side opening 214 of the longitudinal body 202 to engage a lead, the anchor body or both the lead and the anchor body. Such engagement locks the anchor 200 longitudinally in place relative to the lead.

In some embodiments, the longitudinal body 202 may have a circumferential indent 224 to assist suturing of anchor 200 to tissue of the patient. In other embodiments, one or more anchor holes 226 and 228 or other similar structures (such as rib structures) could also be provided in addition to or in place of the circumferential indent 224.

Figure 5:
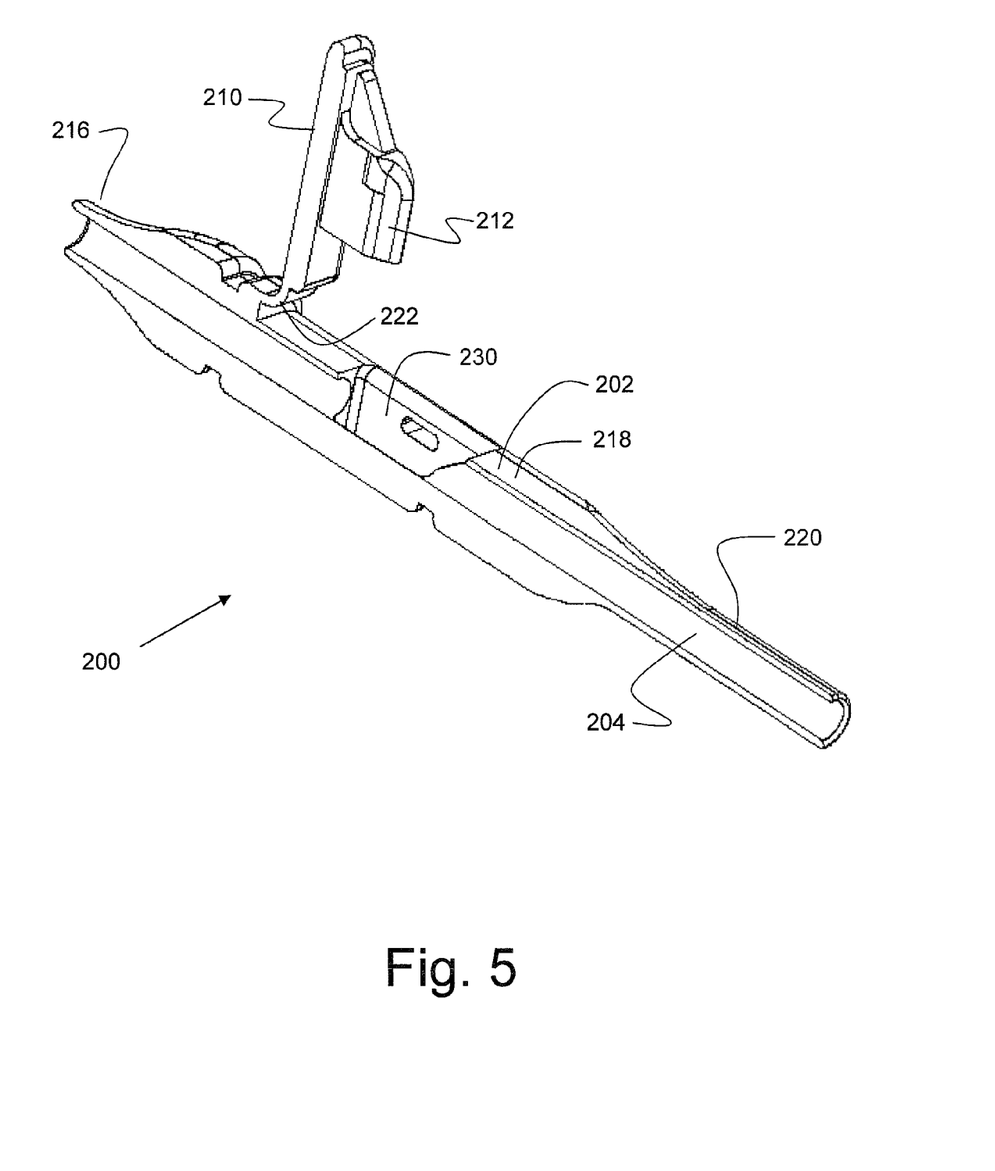
FIG. 5 is a longitudinal cross-sectional view of the embodiment illustrated in FIGS. 4a and 4b.

FIG. 5 is a longitudinal cross-section view of one embodiment of the anchor 200 depicting various components of this embodiment. As illustrated in FIG. 5, it can be seen that the illustrated embodiment of the longitudinal body 202 may comprise a proximal end portion 216, a central body portion 218, and a distal end portion 220. The distal end portion 220 is elongated relative to the proximal end portion 216 which may be useful when implanting or positioning the distal end portion 220 at the implant location.

In certain embodiments, the arm 210 may be coupled to the central portion 218 of the longitudinal body 202 by means of a weakened or flexible portion 222 of the arm 210 occurring at the junction of the arm and the longitudinal body 202. This weakened portion 222 may then function as a hinged member and allow the arm 210 to rotate from the open position illustrated in FIG. 4*a* to the closed position illustrated in FIG. 4*b*. As illustrated, the lumen 204 intersects an interior cavity 230 formed within the central body portion 218. The interior cavity 230 may be sized to receive a portion of the locking finger 212 of the arm 210.

Figure 6A:
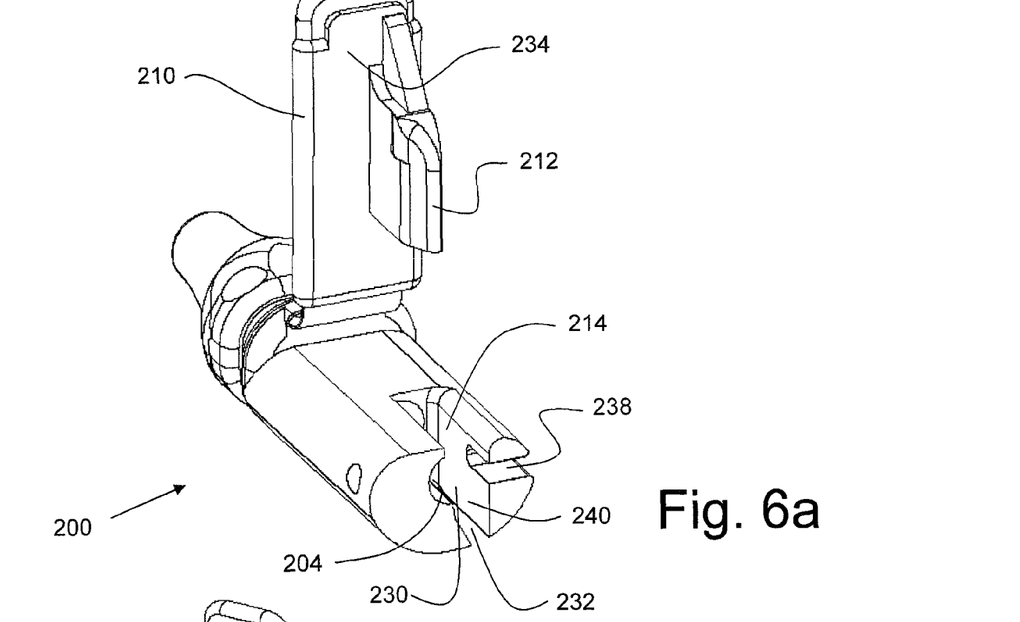
FIG. 6a is a lateral cross-sectional view of the embodiment illustrated in FIG. 4a taken from one side.
Figure 6B:
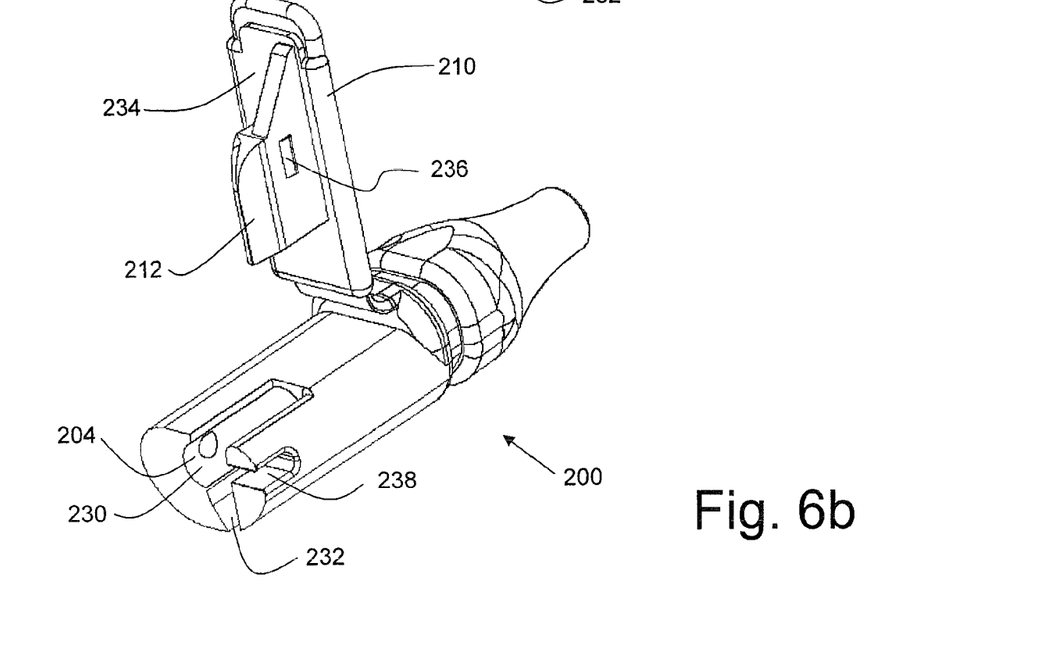
FIG. 6b is a lateral cross-sectional view of the embodiment illustrated in FIG. 4a taken from the other side.

FIG. 6*a* depicts a lateral cross-sectional view of the anchor 200 in the open or unlocked position from the perspective of one side of the anchor. FIG. 6*b* depicts a lateral cross-sectional view of the anchor 200 in the open or un-locked position from the perspective of the other side of the anchor. In the illustrative embodiment, the longitudinal lumen 204 intersects the interior cavity 230.

As previously discussed, the locking finger 212 projects from an interior face 234 of the arm 210. In certain embodiments, the locking finger 212 projects far enough to pass through the side opening 214, through the interior cavity 230 and into a locking opening 232 which, in certain embodiments, runs from the interior cavity 230 out to the side of the longitudinal body 202.

As seen in FIGS. 6*a* and 6*b*, the diameter of the lumen 204 and the size of interior cavity 230 is sufficiently large to permit the introduction of a lead with little difficulty. Thus, when the arm 210 is the open position, the anchor 200 may be freely moved along the leads (not shown). However, when the arm 210 is rotated to the closed position, the finger 212 occupies a portion of the interior cavity 230 and a portion of the space corresponding to the lumen 204. In this closed configuration, therefore, the lumen 204 is now preferably smaller than the diameter of the lead. Thereby, upon rotation of the arm 210 from an open to a closed position, a compressive force is applied to the lead to cause anchor 200 to hold the lead in place. The lead, therefore, cannot be slipped through the anchor 200 along its longitudinal axis.

In certain embodiments, one or more protrusions 236 may be formed on at least one surface of the locking finger 212. A corresponding opening 238 may be defined in an interior surface of the longitudinal body 202 which is positioned and sized such as to catch the protrusion when the locking finger 212 is positioned within the interior cavity 230. Thus, the protrusion 236 may lock the arm 210 in place after the locking finger 212 is placed into the locked position.

Figure 7A:
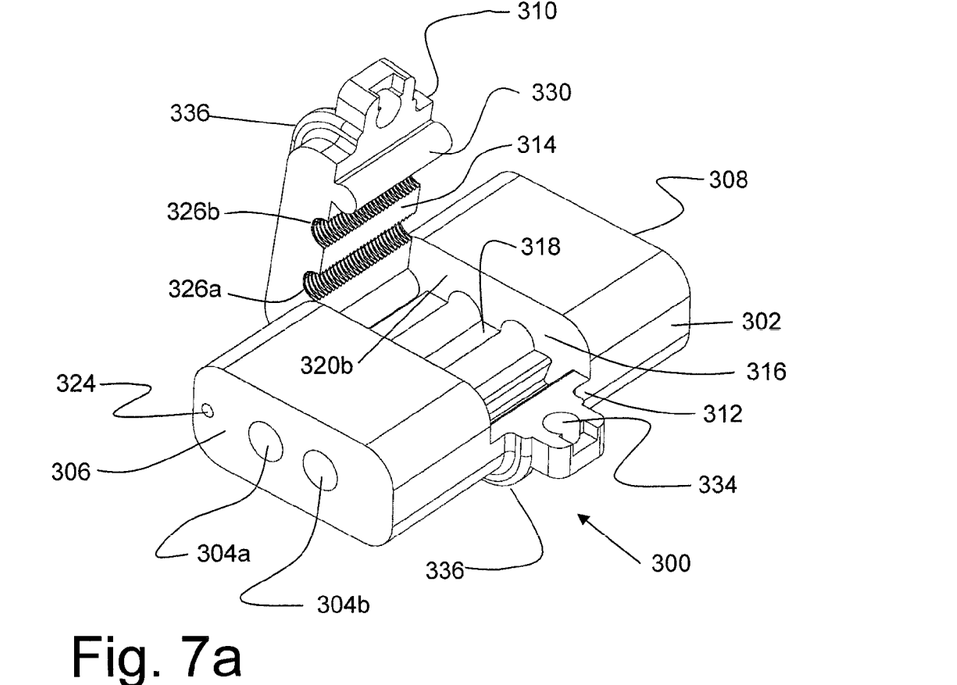
FIG. 7a is an isometric view illustrating one embodiment of an implantable anchor in a first or open configuration.
Figure 7B:
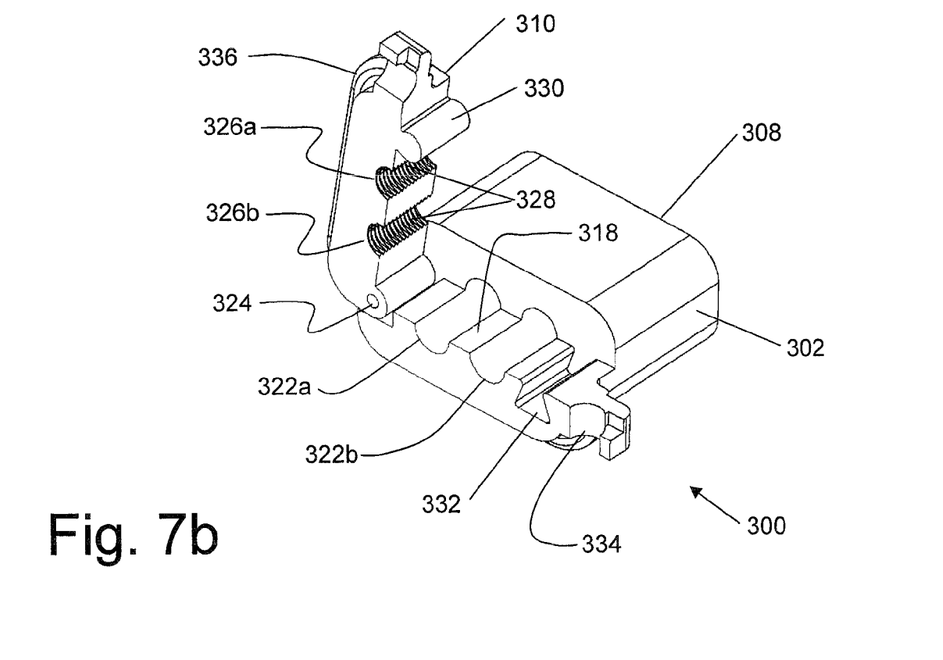

FIGS. 7a and 7b depict an implantable anchor 300 according to an alternative embodiment. FIG. 7a depicts the implantable anchor 300 in a first or open configuration. FIG. 7b depicts a section view of the implantable anchor 300 in the first or open position.

Figure 8A:
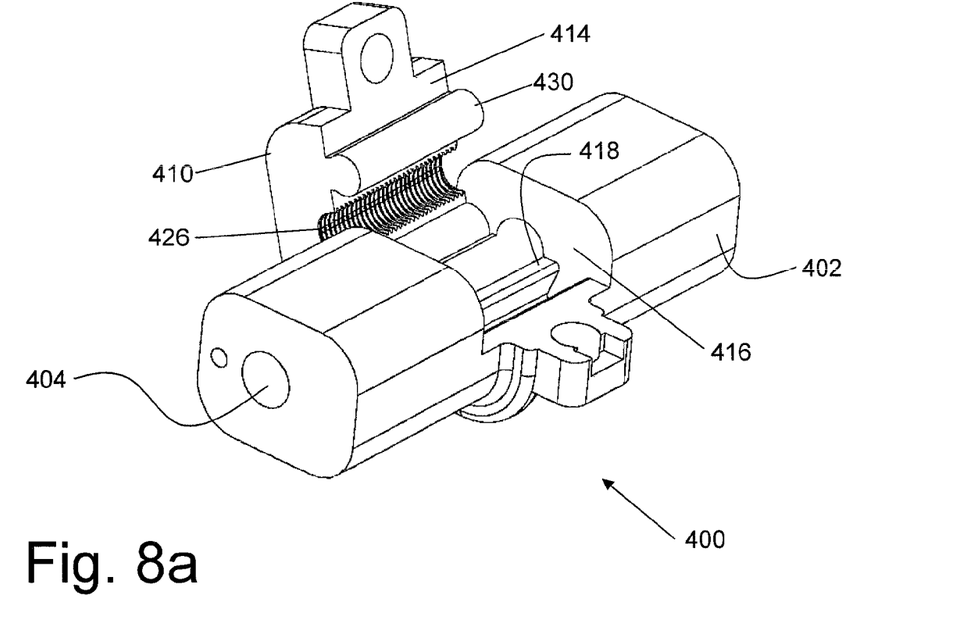
FIG. 8a is an isometric view illustrating one embodiment of an implantable anchor in a first or open configuration.
Figure 8B:
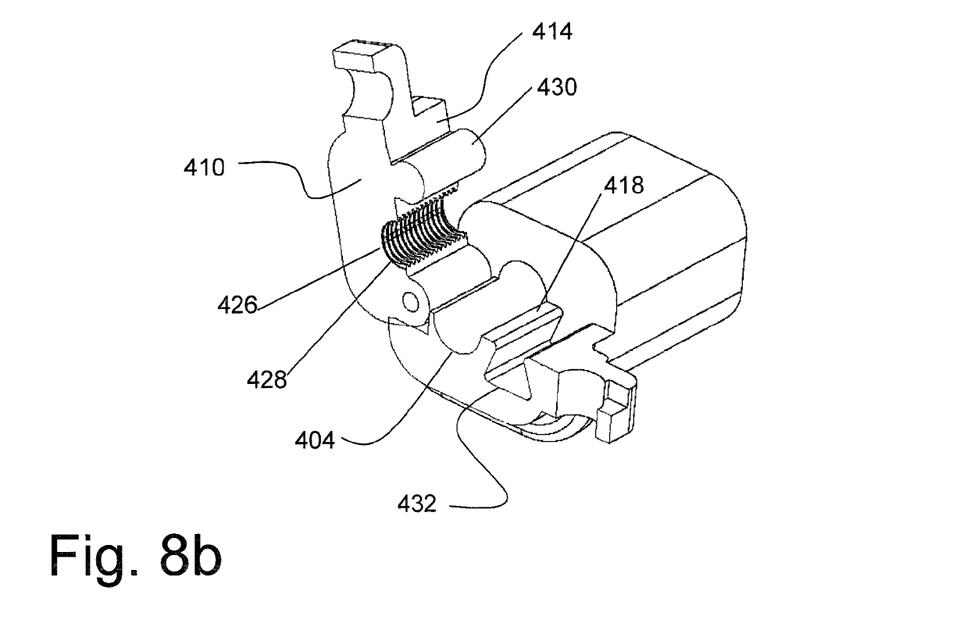

The anchor 300 may comprise an anchor body 302 having one or more longitudinal lumens defined therein. In the illustrative embodiment, two lumens 304a and 304b run longitudinally from a first or proximal end 306 to a second or distal end 308 of the anchor body 302. Although two lumens are illustrated, any number of lumens may be used and are within the scope of the present invention. For instance, FIGS. 8a and 8b depict a locking anchor 400 where there is only one lumen 404.

Returning now to FIGS. 7a and 7b, the diameter of the longitudinal lumens 304a and 304b may be sized to slidingly receive leads (not shown). In use, therefore, the anchor 300 is intended to be placed on the proximal end of two leads and slid over the leads until the anchor 300 is properly positioned along the leads.

As illustrated, a central portion 312 of the body 302 may have a section removed which creates an access opening or access space 316 which partially intersects the lumens 304a and 304b. The access space 316 may be generally defined as the void or opening between a longitudinal surface 318 and two side surfaces 320a and 320b (only side surface 320b is illustrated). In certain embodiments, the longitudinal surface 318 has two semi-circular indentations 322a and 322b (FIG. 7b) which are sized to receive the leads (not shown) and are aligned with the lumens 304a and 304b.

An arm 310 may be moveably coupled to the anchor body 302. In the illustrative embodiment, the arm is shaped to generally fill in the access space 316 when the arm is in a closed position. In certain embodiments, the arm 310 may be coupled to a pin member 324 which may extend along the length of the body 302 in a longitudinal direction. Thus, the arm 310 can rotate about an axis of the pin member 324 which is parallel to the longitudinal axis of the anchor body 302. The arm 310, therefore, can rotate from an open position as illustrated in FIGS. 7a and 7b to a closed position (not shown) in which the arm 310 engages the leads and the anchor body 302. In other embodiments, the arm 310 may be coupled to the central portion 312 of the anchor body 302 by means a weakened or flexible portion of the arm 310 occurring at the junction of the arm and the anchor body 302. This weakened portion may then function as a hinged member and allow the arm 310 to rotate from the open position illustrated in FIGS. 7a and 7b to the closed position.

The arm 310 may include semi-circular indentations 326a and 326b defined on an interior face or surface 314 which are sized to receive a portion of the leads and are positioned to align with semi-circular indentations 322a and 322b when the arm is in a closed position. In certain embodiments, the semi-circular indentations 326a and 326b may have slightly smaller radii than the outer radii of the leads so that a compressive force is placed on each lead when the arm is in the closed position. This compressive force tends to lock the leads in place with respect to the anchor 300. In other embodiments, a plurality of engagement features, such as lateral curved grooves 328 (FIG. 7b) may be defined within the interior surface of the indentations 326a and 326b. These engagement features also prevent longitudinal movement of the leads with respect to the anchor 300 when the arm 310 is in the closed position.

The diameters of the lumens 304a and 304b and the size of access space 316 are sufficiently large to permit the introduction of a lead with little difficulty. Thus, when the arm 310 is the open position, the anchor 300 may be freely moved along the leads (not shown). In this closed configuration, however, the lumens 304a and 304b are now preferably smaller than the diameter of the lead. Thereby, upon rotation of the arm 310 from an open to a closed position, a compressive force is applied to the leads to cause anchor 300 to hold the leads in place. The leads, therefore, cannot be slipped through the anchor 300 along its longitudinal axis.

A locking feature may also be defined on the arm 310. The locking feature may be sized to engage a corresponding locking feature defined within the anchor body 302. For instance, in the illustrative embodiment, a cylindrical protrusion 330 extends longitudinally along an interior surface or face 314 of the arm 310. A corresponding dovetailed groove 332 (FIG. 7b) may be defined in the surface 318. Thus, in the closed position, the cylindrical protrusion 330 engages and is received by the dovetail groove 332. In certain embodiments, the diameter of the cylindrical protrusion 330 is larger than the opening of the dovetail groove 332. So, when the user forces the cylindrical protrusion 330 in place, the cylindrical protrusion is restrained and the arm 310 is locked into the closed position.

One or more anchor holes and/or other structures such as circumferential rib structures may be provided assist suturing of anchor 300 to tissue of the patient. For instance, an anchoring hole 334 may run through both the arm 310 and the center section 312. One or more rib features 336 may also be defined on the center portion 312.

FIGS. 8a and 8b depict the locking anchor 400 according to an alternative embodiment. The anchor 400 preferably functions in a manner similar to the anchor 300 and, hence, details of the components and functions of the anchor 400 will not be discussed here. In general, the anchor 400 differs from the anchor 300 in that the anchor 400 has a single longitudinal lumen and is meant to anchor a single lead (not shown). Thus, the anchor 400 comprises an anchor body 402 having a first longitudinal lumen 404 sized to receive a medical lead (not shown), an access opening or space 416 defined within a side of the anchor body 402 and intersecting the longitudinal lumen 404 (FIG. 8a). There may be a locking opening or dovetail groove 432 defined on an interior surface 418 of the anchor body 402 and an arm 410 having an interior face or surface 414. The arm 410 is moveably coupled to the anchor body 402 such that the arm is movable from a first position in which the arm covers or fills the access space 416 to a second position in which the arm does not cover the access space. There may also be a locking feature, such as cylindrical protrusion 430 protruding from the interior face 414 of the arm 410 and sized to extend through the access opening or access space 416 and into the locking opening 432 to engage the locking opening. In certain embodiments, there may be a plurality of surface features, such as a cylindrical indention 426 having lateral curved groves 428 defined on the interior face 414 of the arm 410 for restraining the movement of the medical lead relative to the anchor body 402.

Anchors according to representative embodiments may be utilized in conjunction with any suitable implantable medical device that comprises an implantable lead. For example, anchors 100 through 400 can be utilized to anchor a stimulation lead of a neurostimulation system as shown in FIG. 9. A neurostimulation system 500 includes a pulse generator 502 and one or more stimulation leads 504. An example of a commercially available pulse generator is the EON® product available from Advanced Neuromodulation Systems, Inc. An example of a commercially available stimulation lead is the Axxess® lead available from Advanced Neuromodulation Systems, Inc.

The pulse generator 502 is typically implemented using a metallic housing that encloses circuitry for generating the electrical pulses for application to neural tissue of the patient. The pulse generator 502 is usually implanted within a subcutaneous pocket created under the skin by a physician. The lead 504 is used to conduct the electrical pulses from the implant site of the pulse generator for application to the targeted nerve tissue via electrodes 506. The lead 504 typically includes a lead body of an insulative polymer material with embedded wire conductors extending through the lead body. The electrodes 506 of the lead body are coupled to the conductors to deliver the electrical pulses to the nerve tissue. For example, the distal end 508 of lead 504 may be positioned within the epidural space of the patient to deliver electrical stimulation to spinal nerves to treat chronic pain of the patient. The anchors 100 through 400 may be utilized to ensure that the distal end 508 of the lead 504 remains adjacent to the appropriate nerves associated with the chronic pain of the patient. In some embodiments, an "extension" lead (not shown) may be utilized as an intermediate connector if deemed appropriate by the physician.

In certain embodiments for SCS applications, the lead 504 is a "body compliant" lead that possesses mechanical characteristics that allow the lead 504 to stretch in response to forces experienced with the patient's body. For example, the lead 504 may be adapted to stretch up to 25% in response to low stretching forces such as 2-2 pounds of force. The ability to exhibit significant elongation in response to such low forces enables the lead to be relatively robust (e.g., does not experience significant conductor breakage). Fabrication techniques and material characteristics for "body compliant" leads are disclosed in greater detail in U.S. Provisional Patent Application Ser. No. 60/788,518, entitled "Lead Body Manufacturing," filed Mar. 31, 2006, which is incorporated herein by reference for all purposes.

Alternatively, the anchors 100 through 400 can be utilized to anchor an infusion catheter of an implantable drug infusion device 600 as shown in FIG. 10. The implantable infusion drug pump device 600 may include a central housing 602, a reservoir 604 to hold the infusate, a septum 606 to allow infusate to be introduced into the reservoir, an energy source 608 (e.g., a spring diaphragm) to drive the infusate from the reservoir and through an outlet port 610, and various flow control elements (not shown).

The central housing 602 of the device is often implanted in a suitable subcutaneous region with the septum 606 positioned immediately below the skin of the patient to facilitate access to the reservoir 604 for refilling purposes. A catheter 612 is attached to the outlet port 610 of the central housing 602 to receive the infusate outflow. A distal end 614 of the catheter is implanted within the patient adjacent to the appropriate therapy site. The anchors 100 through 400 may be utilized to ensure that the distal end 614 of the lead 612 remains adjacent to the appropriate site generating the chronic pain of the patient.

Although some representative embodiments have been discussed in terms of anchoring intrathecal and epidural catheters and leads, anchors can be employed according to alternative embodiments for any suitable location. For example, an anchor according to some embodiments could be used for peripheral nerve stimulation and gastric pacing applications.

In another example, there may be an implantable medical system comprising: an implantable pulse generator having pulse generation circuitry and a plurality of electrical connectors, at least one lead including a longitudinal body of compliant material having a proximal end portion and a distal end portion; a plurality of terminal electrodes longitudinally positioned along the proximal end portion such that the terminal electrodes are removably connected to the plurality of electrical connectors, a plurality of stimulation electrodes longitudinally positioned along the distal end portion electrically coupled to the plurality of electrical connectors, an implantable anchor coupled to the at least one lead, the implantable anchor comprising: a body having a longitudinal lumen for receiving the lead, an access opening defined within a side of the body and in communication with the lumen, a locking opening defined on an interior surface of the body, an arm having an interior face, the arm rotatably coupled to the longitudinal body such that the arm is movable from a first position in which the arm covers the access opening to a second position in which the arm does not cover the access opening, and a locking finger protruding from the interior face of the arm and sized to extend into the locking opening.

In another example, there may be an implantable medical system comprising: an implantable medical device, at least one catheter coupled to the implantable medical device wherein the at least one catheter is for applying medical therapy, and an implantable anchor coupled to the at least one catheter, the implantable anchor comprising: a body having a longitudinal lumen for receiving the catheter, an access opening defined within a side of the body and in communication with the lumen, a locking opening defined on an interior surface of the body, an arm having an interior face, the arm rotatably coupled to the longitudinal body such that the arm is movable from a first position in which the arm covers the access opening to a second position in which the arm does not cover the access opening, and a locking finger protruding from the interior face of the arm and sized to extend into the locking opening.

In yet another example, there may be a medical system comprising: an implantable infusion drug pump, at least one catheter coupled to an outlet port of the implantable infusion drug pump to receive infusate outflow and an implantable anchor coupled to the at least one catheter, the implantable anchor comprising: a body having a longitudinal lumen for receiving the catheter, an access opening defined within a side of the body and in communication with the lumen, a locking opening defined on an interior surface of the body, an arm having an interior face, the arm rotatably coupled to the longitudinal body such that the arm is movable from a first position in which the arm covers the access opening to a second position in which the arm does not cover the access opening, and a locking finger protruding from the interior face of the arm and sized to extend into the locking opening.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure that processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

Any combination of the features discussed above are within the scope of certain embodiments of the present invention. Thus, a feature disclosed in reference to one embodiment may be combined with another embodiment. Furthermore, combinations of disclosed features and alternative features are within the scope of certain embodiments of the present invention.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

What is claimed is:

1. An implantable anchor for permanently anchoring a medical lead, the anchor comprising:
    a body having a longitudinal lumen;
    an access opening defined within a side of the body and in communication with the longitudinal lumen;
    a locking opening defined on an interior surface of the body;
    an arm having an interior face, the arm rotatably coupled to the body such that the arm is movable from a first position in which the arm covers the access opening to a second position in which the arm does not cover the access opening;
    a locking feature protruding from the interior face of the arm and sized to extend into the locking opening; and
    an engagement mechanism defined on a surface of the locking feature and adapted to engage a surface to lock the locking feature in place when a portion of the locking feature is positioned into the access opening, the engagement mechanism including a locking indent adapted to engage the medical lead.

2. The implantable anchor of claim 1, further comprising a second lumen in communication with the access opening.

3. The implantable anchor of claim 1 wherein the arm is coupled to the body with a pin.

4. The implantable anchor of claim 1 wherein the arm is coupled to the body with a flexible body portion.

5. The implantable anchor of claim 1, wherein the arm rotates about an axis which is generally transverse to a longitudinal axis of the body.

6. The implantable anchor of claim 1, further comprising:
    a locking indent defined within the interior surface of the body; and
    wherein the engagement mechanism comprises a protrusion adapted to engage the locking indent.

7. The implantable anchor of claim 1, further comprising an interior cavity intersecting the lumen and sized to house a portion of the locking feature.

8. The implantable anchor of claim 7, wherein the locking opening extends from the interior cavity to an exterior side of the body.

9. The implantable anchor of claim 1, wherein the body comprises:
    a first strain relief portion having a first strain relief lumen;
    a second strain relief portion having a second strain relief lumen; and
    a center portion housing the longitudinal lumen and coupled to the first strain relief portion on a first end and coupled to the second strain relief portion on a second end such that the first strain relief lumen and the second strain relief lumen are longitudinally aligned with the longitudinal lumen.

10. The implantable anchor of claim 9, wherein the first strain relief portion and the second strain relief portion are formed from a first material and the center portion is formed from a second material, and the first material is flexible relative to the second material.

11. The implantable anchor of claim 1, wherein the arm rotates about an axis which is generally parallel to a longitudinal axis of the body.

12. The implantable anchor of claim 1, further comprising features defined in the interior surface sized to engage the surface of the lead such that the lead is restrained relative to the body.

13. The implantable anchor of claim 1 further comprising:
    a first bore defined within a portion of the body proximal to the access opening, and
    a second bore defined within the arm and aligned with the first bore when the arm is in the first position to facilitate suturing of the implantable anchor to tissue.

14. An implantable anchor for permanently anchoring a medical lead comprising:
    a longitudinal body having a first longitudinal lumen and a second longitudinal lumen;
    an interior cavity defined within the longitudinal body intersecting the first lumen and the second lumen;
    an access opening defined within a side of the longitudinal body in communication with the first and second lumen;
    an arm having an interior face, the arm moveably coupled to the longitudinal body such that the arm is movable from a first position in which the arm covers the access opening to a second position in which the arm does not cover the access opening; and
    a locking finger protruding from the interior face of the arm and sized to extend through the access opening and into the interior cavity to engage a surface of a lead, wherein the locking finger includes an engagement mechanism to secure the position of the finger relative to the longitudinal body, the engagement mechanism including at least one locking indent defined on a surface of the locking finger and adapted to engage a compliant surface of the lead.

15. The implantable anchor of claim 14, further comprising a locking opening defined within the interior cavity on a surface opposed to the access opening, and wherein the locking finger is sized to extend through the interior cavity and into the locking opening.

16. The implantable anchor of claim 14, further comprising:
    a locking indent defined within an interior surface of the longitudinal body and in communication with the first and second lumens; and
    wherein the engagement mechanism comprises a protrusion adapted to engage the locking indent.

17. An implantable anchor for permanently anchoring a medical lead comprising:
    a body having a first longitudinal lumen sized to receive the medical lead;
    an access opening defined within a side of the body intersecting the first longitudinal lumen;
    a locking opening defined on an interior surface of the body;
    an arm having an interior face, the arm moveably coupled to the body such that the arm is movable from a first position in which the arm covers the access opening to a second position in which the arm does not cover the access opening;

a locking feature protruding from the interior face of the arm and sized to extend through the access opening and into the locking opening to engage the locking opening;

a plurality of surface features defined on the interior face of the arm for restraining the movement of the medical lead relative to the body;

a first bore defined within a portion of the body proximal to the access opening; and a second bore defined within the arm, and when the arm is in the first position, is aligned with the first bore creating a feature to facilitate suturing of the implantable anchor to tissue.

18. The implantable anchor of claim 17, wherein the arm rotates about an axis which is generally parallel to a longitudinal axis of the body.

19. The implantable anchor of claim 17, further comprising a second longitudinal lumen defined within the body sized to receive a medical lead.

* * * * *